United States Patent [19]
Gadelle et al.

[11] 4,088,734

[45] May 9, 1978

[54] REMOVAL OF HYDROGEN ARSENIDE

[75] Inventors: Claude Gadelle, Rueil-Malmaison; Jean-Pierre Laloz, Marly le Roi; Irenee Seree de Roch, Rueil-Malmaison, all of France

[73] Assignee: Institut Francais du Petrole, Rueil-Malmaison, France

[21] Appl. No.: 748,410

[22] Filed: Dec. 8, 1976

[30] Foreign Application Priority Data

Dec. 8, 1975 France .................................. 75 37717

[51] Int. Cl.$^2$ ............................................. B01D 53/34
[52] U.S. Cl. ....................................... 423/210; 55/68; 55/72
[58] Field of Search ................... 423/210, 220; 55/72, 55/68

[56] References Cited

U.S. PATENT DOCUMENTS

1,519,470  12/1924  Wilson et al. ....................... 423/210

FOREIGN PATENT DOCUMENTS

117,293  1/1966  Czechoslovakia ................... 423/210

OTHER PUBLICATIONS

Mellor, "A Comprehensive Treatise on Inorganic & Theoretical Chemistry," Longman, Green & Co., New York, N. Y. vol. 9, 1929, pp. 58 & 69.

*Primary Examiner*—Earl C. Thomas
*Attorney, Agent, or Firm*—Millen & White

[57] ABSTRACT

Process for removing arsenic compounds and particularly arsine from gases containing the same, by treating said gases with a washing solution consisting either of an alkaline aqueous solution, containing a zinc or lead, salt or oxide and/or one or more salts of anthraquinone sulfonic or disulfonic acids, or of a solution in an organic solvent of at least one quinone compound in the presence of an amine or an ethanolamine.

16 Claims, No Drawings

REMOVAL OF HYDROGEN ARSENIDE

This invention concerns a purification process for removing volatile arsenide compounds and particularly hydrogene arsenide $H_3As$. The process of the invention is particularly useful for the purification of gaseous saturated, olefinic, conjugated diolefinic and acetylenic hydrocarbons and their mixtures, or for the purification of mixtures of gaseous hydrocarbons with permanent gases.

The process of the invention consists of treating the gaseous effluent containing the arsenide impurity either with an alkaline aqueous solution of at least one metal salt or oxide, or with an alkaline aqueous solution of at least one salt of anthraquinone sulfonic or disulfonic acid (anthraquinone sulfonate), or with a solution based on an organic solvent containing at least one quinone compound in the presence of an amine, particularly an ethanolamine.

In the first case, the alkaline aqueous solution will be a sodium hydroxide or potassium hydroxide solution, whose sodium hydroxide or potassium hydroxide content is from 1 to 20% by weight. The metal of the salt or oxide will be lead or zinc. The metal will have preferably an oxidation degree of 2. The metal content of the alkaline solution, depending on the concentration of sodium hydroxide or potassium hydroxide, is from about 0.01% to 10% by weight, preferably from 0.5 to 4%.

In the second case, the alkaline aqueous solution will be maintained at a pH from about 7.0 to 11 and preferably from about 7.5 to 9.7. It will be possible, for example, to make use of solutions of sodium bicarbonate or sodium tetraborate in the presence or absence of boric acid. The anthraquinonesulfonates suitable for the process of the invention are hydrosoluble salts of the known isomers of the anthraquinone sulfonic and anthraquinone disulfonic acids and their mixtures, particularly 9,10-anthraquinone-2,7-disulfonic, 9,10-anthraquinone-1,5-disulfonic and 9,10-anthraquinone-2,6-disulfonic acids. The content of hydrosoluble salt may be at least about 0.01% b.w. and may range up to 15% by weight for the most soluble compounds.

In the third case, the organic solvent may be selected from alcohols, ketones, ethers, esters, glycols and polyethers.

The following are non-limitative examples of solvents in each family:

Alcohols: methanol, ethanol, butanols, propyleneglycol, glycol, ethylhexanol, etc...

Ketones: acetone, methylethylketone, cyclohexanone, acetophenone, etc...

Esters: acetates, propionates, butyrates, phthalates, phosphates, etc...

Ethers: butyl ether, isopropyl ether, dioxane, polyethyleneglycols, polypropylene glycols, etc...

Polyethylene glycol 400 for example, in view of its low vapor pressure, is a preferred solvent. The amines may be either primary, secondary or tertiary.

The amines used in the process comply with the general formulas:

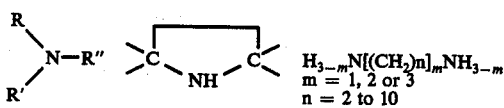

One or two of the radicals R, R' and R" may be hydrogen atoms (primary amines, secondary amines), the radicals R,R' and R" being as a general rule, identical, different or mixed aliphatic or aromatic radicals.

By way of non limitative examples, the following amines may be mentioned: ethylamine, propylamine, isopropylamine, butylamine, hexylamine, octylamine, diethylamine, dipropylamine, diisopropylamine, dibutylamine, dihexylamine, dioctylamine, monoethanolamine, diethanolamine, triethanolamine, diethylenediamine, triethylenediamine, aniline, toluidines, xylidines, diphenylaniline, diethylaniline, morpholine, piperidine, ethylphenylaniline ...

The ethanolamines are, for example, quite suitable, in view of their low vapor pressure and their availibility on the market. The quinones used in the process are for example benzoquinone and 2-ethyl anthraquinone which are available on the market.

By way of non-limitative examples, the following may be mentioned : benzoquinone, 2-ethyl anthraquinone, α-naphthoquinone, β-naphthoquinone etc ... The amine content of the organic washing solution will be from 0.1 to 10% by weight; the quinone content, limited by its solubility, will be higher than 0.01% by weight.

In the three considered cases, the treatment temperature for the effluent subjected to purification will be from about 0° to 100° C; the absolute pressure will be from about 0.1 to 50 bars. Preferably, the operating conditions will be as follows: temperature from 20° to 60° C and pressure from 1 to 20 bars or, more preferably, from 8 to 18 bars.

The treatment will be preferably performed countercurrently in a column provided with plates and/or inert packing.

The following non-limitative examples illustrate the invention. In all cases, the determination of arsine in the effluent has been performed according to the method proposed by G. W. POWERS, R. L. MARTIN, F. J. PIEHL, J. M. GRIEFFIN, Anal. Chem. 31, 1589–1959. The U.V. absorption has been measured at 340 mm (nanometers; 1 mm = $10^{-9}$ meter) by using a spectrophotometer Perkin Elmer type 402. The measuring cell being 1cm thick, for an arsenic content of 0.334 γ per cc, the average variation of optic density is 0.07 units.

Washings have been performed in a column containing a packing (Raschig rings). The volume of washing solution is, in all cases, 100cc. The velocities per volume and per hour (VVH) expressed with reference to said volume, are indicated for normal conditions of temperature and pressure.

EXAMPLE 1

There is used an aqueous solution containing 10% by weight of sodium hydroxide. The metal involved is lead, used successively in the form of acetate : Pb[$CH_3COO$]$_2$ 3H$_2$O, nitrate: Pb(NO$_3$)$_2$ and oxide : PbO. The lead content of the solution is 1% by weight. The effluent to be purified consists of a mixture of ethylene and hydrogen containing 80% by volume of ethylene and whose H$_3$As content is 0.68 γl$^{-1}$.(1 γ = 1 μg = $10^{-6}$ g).

The operating conditions are as follows:
pressure: 15 bars
temperature: 40° C
duration: 6 h.
V.V.H: 8, 000

In these condition, the arsine removal rate is higher than 95% irrespective of the lead compound used.

EXAMPLE 2

Example 1 is repeated, the effluent being however constituted by a mixture having the following molar composition, expressed in percents:
Hydrogen — 2
Methane — 4
Ethylene — 62
Butadiene — 3
Acetylene — 2
Propylene — 27

The arsine content at the inlet of the washing reactor is 0.57 $\gamma l^{-1}$; it is lower than 0.01 $\gamma l^{-1}$ after the treatment.

EXAMPLE 3

The washing step is performed with an alkaline solution having a NaOH content of 15% by weight and containing 1% by weight of zinc, introduced in the form of zinc oxide: ZnO. The effluent to be purified consists of a mixture of nitrogen with ethylene, having a 40% nitrogen content by volume and a $H_3As$ content of 0.830 $\gamma l^{-1}$.

The operating conditions were as follows:
Pressure: 10 bars
Temperature: 40° C
Duration: 4 h.
V.V.H: 2.500

The arsine removal rate was 75%.

EXAMPLE 4

Polyethylene glycol 400 is used as solvent. The washing solution contains 3% by weight of diethanolamine and 0.9% by weight of 2-ethyl anthraquinone. In the same operating conditions as in example 1 and with the same effluent subjected to purification, the arsine removal rate was higher than 90%.

EXAMPLE 5

The washing aqueous solution is a solution of sodium anthraquinone disulfonate corresponding to the 2,7-isomer and of sodium tetraborate ($Na_2B_4O_7$). The composition of the solution is as follows:

| anthraquinone disulfonate | 1.15 % by weight |
|---|---|
| sodium tetraborate | 0.5 % by weight |

The effluent to be purified consists of propane containing 0.48 $\gamma l^{-1}$ of arsine.

The washing conditions were as follows:
Pressure: 17 bars
Temperature: 50° C
Duration: 4 h.
V.V.H.: 3 500

At the outlet from the washing reactor, the arsine content of the gaseous effluent was lower than 0.03 $\gamma l^{-1}$.

EXAMPLE 6

This example comprises the use of a sodium hydroxide aqueous solution containing 10% by weight of sodium hydroxide and 1% by weight of lead introduced in the form of lead oxide: PbO (yellow β form).

The effluent to be purified consists of a $C_4$ steamcracking cut having the following molar composition:

|  | % mol. |
|---|---|
| Hydrogen | 12.5 |
| Methane | 26.8 |
| Acetylene | 2.4 |
| Ethylene | 29 |
| Ethane | 6.6 |
| Methylacetylene | 2.3 |
| Propane | 2 |
| Propylene | 11.5 |
| Butadiene | 2.1 |
| Butenes | 2.8 |
| Butane | 1.5 |
| Butyne | 0.4 |

The $H_3As$ content is 0.7 $\gamma l^{-1}$.
The operating conditions are as follows:
Pressure: 15 bars
Temperature: 40° C
Duration: 8 h.
V.V.H.: 8.000

In these conditions, the arsine removal rate was 97.3% By repeating this example with the same alkaline solution containing 1% of zinc introduced in the form of ZnO, the arsine removal rate was 82%.

What we claim is:

1. A process for removing hydrogen arsenide $H_3As$ from a gaseous effluent containing hydrogen arsenide as an impurity, wherein the gaseous effluent is washed at a temperature between 0° and 100° C, with an aqueous washing solution containing sodium hydroxide or potassium hydroxide, at least one salt or oxide of zinc or lead, the concentration of sodium hydroxide or potassium hydroxide being from 1 to 20% by weight of the said washing solution, and the zinc or lead content being from 0.01 to 10% by weight of the said solution.

2. A process according to claim 1, wherein the zinc or lead content is from 0.5 to 4% by weight of the solution.

3. A process according to claim 1, wherein zinc is used.

4. A process according to claim 1, wherein the gaseous effluent is predominantly hydrocarbon.

5. A process according to claim 1, wherein lead is used.

6. A process for removing hydrogen arsenide $H_3As$ from a gaseous effluent containing hydrogen arsenide as an impurity, wherein the gaseous effluent is washed, at a temperature between 0° and 100° C, with an aqueous alkaline washing solution of at least one salt of a sulfonic or disulfonic anthraquinone acid.

7. A process according to claim 6, wherein the pH of said alkaline aqueous solution of at least one salt of a sulfonic or disulfonic anthraquinone acid is from about 7.0 to 11.

8. A process according to claim 7, performed in the presence of sodium bicarbonate or tetraborate and a sodium salt of anthraquinone sulfonic acids, either pure or as mixtures.

9. A process according to claim 6, wherein the salt of a sulfonic or disulfonic anthraquinone acid is selected from the hydrosoluble salts of 9,10-anthraquinone-2,7-disulfonic, 9,10-anthraquinone-1,5-disulfonic and 9,10-anthraquinone-2,6-disulfonic acids.

10. A process according to claim 6, wherein the gaseous effluent is predominantly hydrocarbon.

11. A process for removing hydrogen arsenide $H_3As$ from a gaseous effluent containing hydrogen arsenide as an impurity, wherein the gaseous effluent is washed, at a temperature between 0° and 100° C, with a washing solution consisting essentially of an organic solvent containing at least one quinone compound and a hydrocarbon amine or an ethanolamine.

12. A process according to claim 11, wherein the organic solvent containing at least one quinone compound is selected from the alcohols, ketones, ethers, glycols, ethers and polyethers.

13. A process according to claim 11, containing said hydrocarbon amine which is a primary, secondary or tertiary amine, the amine content being from about 0.1 to 10% by weight of the organic solvent.

14. A process according to claim 11, wherein said ethanolamine is used at a concentration from about 0.1 to 10% by weight of the organic solvent.

15. A process according to claim 12, wherein the polyether is polyethyleneglycol 400.

16. A process according to claim 11, wherein the gaseous effluent is predominantly hydrocarbon.

* * * * *